(12) United States Patent
Herskovic

(10) Patent No.: US 10,420,956 B2
(45) Date of Patent: Sep. 24, 2019

(54) DEVICE AND METHOD FOR DELIVERING MEDICAMENTS

(71) Applicant: BOSTON SCIENTIFIC CORPORATION, Natick, MA (US)

(72) Inventor: Arnold M. Herskovic, Chicago, IL (US)

(73) Assignee: BOSTON SCIENTIFIC CORPORATION, Marlborough, MA (US)

( * ) Notice: Subject to any disclaimer, the term of this patent is extended or adjusted under 35 U.S.C. 154(b) by 228 days.

(21) Appl. No.: 14/849,523

(22) Filed: Sep. 9, 2015

(65) Prior Publication Data

US 2015/0375012 A1    Dec. 31, 2015

Related U.S. Application Data

(63) Continuation of application No. PCT/US2014/030157, filed on Mar. 17, 2014.

(60) Provisional application No. 61/798,171, filed on Mar. 15, 2013.

(51) Int. Cl.
| | | |
|---|---|---|
| *A61N 5/10* | (2006.01) | |
| *A61M 37/00* | (2006.01) | |
| *A61B 6/00* | (2006.01) | |
| *A61M 25/10* | (2013.01) | |
| *A61B 90/00* | (2016.01) | |

(52) U.S. Cl.
CPC ............ *A61N 5/1007* (2013.01); *A61B 6/481* (2013.01); *A61B 6/486* (2013.01); *A61B 90/39* (2016.02); *A61M 25/10* (2013.01); *A61M 37/0069* (2013.01); *A61N 5/1015* (2013.01); *A61N 5/1048* (2013.01); *A61B 2090/3966* (2016.02); *A61M 2025/105* (2013.01); *A61N 2005/1011* (2013.01); *A61N 2005/1098* (2013.01)

(58) Field of Classification Search
CPC .............................................. A61N 5/10–1027
See application file for complete search history.

(56) References Cited

U.S. PATENT DOCUMENTS

| | | | |
|---|---|---|---|
| 5,871,708 | A | 2/1999 | Park et al. |
| 6,132,359 | A | 10/2000 | Bolenbaugh |
| 6,248,057 | B1 | 6/2001 | Mavity et al. |
| 6,575,888 | B2 | 6/2003 | Zamora et al. |
| 6,589,502 | B1 | 7/2003 | Coniglione |
| 6,746,661 | B2 | 6/2004 | Kaplan |
| 6,749,553 | B2 | 6/2004 | Brauckman et al. |
| 7,011,619 | B1 * | 3/2006 | Lewis ................. A61N 5/1027 600/1 |
| 7,252,630 | B2 | 8/2007 | Terwilliger et al. |
| 7,776,310 | B2 | 8/2010 | Kaplan |

(Continued)

FOREIGN PATENT DOCUMENTS

| | | |
|---|---|---|
| CN | 201643386 U | 11/2010 |
| WO | 2011015958 A2 | 2/2011 |

*Primary Examiner* — Thaddeus B Cox

(74) *Attorney, Agent, or Firm* — Seager, Tufte & Wickhem, LLP

(57) ABSTRACT

A medicament delivery vehicle, the vehicle comprising a reversibly deformable carrier (RDC) adapted to support the medicament on an outside surface of the carrier, an inside surface of the carrier, or homogeneously dispersed throughout the carrier. Specifically, the medicament delivery device may include a reversibly deformable carrier (RDC) adapted to support the medicament.

18 Claims, 1 Drawing Sheet

(56) References Cited

U.S. PATENT DOCUMENTS

| | | | |
|---|---|---|---|
| 7,922,646 B2 | 4/2011 | Russell, Jr. et al. | |
| 8,827,884 B2 | 9/2014 | Ribbing et al. | |
| 2002/0058057 A1* | 5/2002 | Kaplan | A61K 41/0038 |
| | | | 424/426 |
| 2003/0120355 A1 | 6/2003 | Hafeli et al. | |
| 2004/0109823 A1 | 6/2004 | Kaplan | |
| 2008/0045773 A1* | 2/2008 | Popowski | A61N 5/1015 |
| | | | 600/4 |
| 2008/0071132 A1* | 3/2008 | Lamoureux | A61N 5/1015 |
| | | | 600/7 |
| 2008/0194985 A1* | 8/2008 | Nicoson | A61B 10/0275 |
| | | | 600/566 |
| 2008/0281388 A1 | 11/2008 | Corbitt et al. | |
| 2010/0056843 A1 | 3/2010 | Fisher et al. | |
| 2011/0142936 A1* | 6/2011 | Campbell | A61L 27/50 |
| | | | 424/484 |
| 2012/0123189 A1 | 5/2012 | Ribbing et al. | |

* cited by examiner

DEVICE AND METHOD FOR DELIVERING MEDICAMENTS

CROSS-REFERENCE TO RELATED APPLICATIONS

This application is a continuation of PCT Application No. PCT/US2014/030157, filed Mar. 17, 2014 which claims priority to U.S. Provisional Application Ser. No. 61/798,171, filed Mar. 15, 2013, the entire disclosures of which are incorporated herein by reference.

FIELD OF INVENTION

The present invention relates to a device and method for delivering medicaments and more particularly, the present invention relates to a device and a method for treating cancers and tumors with radiation.

BACKGROUND

Some cancers and neoplasms are easier to treat with radiation than others. Hard-to-reach (or safely treat) neoplasms, such as those in the esophagus, intestines and other lumens, are often treated via Brachytherapy (use of radioactive particles, commonly known as seeds) so as to minimize radiation to adjacent, healthy tissue.

The radiation (dose distribution) depends on geometry especially the inverse square law, filtration by encapsulation material, and also adsorption in tissue and air. Individual seeds are shielded by the encapsulation process which usually limits the useful exposure to a short range of x or gamma rays. The initial dose rate would vary inversely with halve life. As an example, the typical initial dose rate for an Iodine 125 prostate implant would usually be about 0.07 Gy/hr (7 rad per hour) as opposed to about 20 for Palladium 103. Host factors such as oxygenation, intrinsic radio sensitivity proliferation rate repair capacity are more difficult to control.

Brachytherapy delivers radiation to small tissue volumes while limiting exposure of healthy tissue. In this regard, the delivered radiation conforms more to the target than any other form of radiation, (including proton therapy) as less normal transient tissue is treated. It features placement of radiation sources, such as small radioactive particles (usually as encapsulated seeds directly or in tubes or needles) near or within the target tissue, thus having the advantage over External Beam Radiation Therapy (EBRT) of being more focalized and less damaging to surrounding healthy tissue.

Brachytherapy is a common treatment for esophageal, prostate, and other cancers. Approximately 15,000 and 480,000 cases of esophageal cancer are diagnosed in the U.S. and worldwide, respectively. At least 50 percent fail locally who present with curable cancers, which is to say that 50 percent suffer from persistence or recurrence of the cancers at the original cancer site. (Esophageal cancer treatment is a reasonable prototype for luminal brachytherapy that could be expanded to other sites.)

Brachytherapy can be delivered in several rates: a Low-Dose Rate (LDR, or less than 2 Gy/hr), a High-Dose Rate (HDR or greater than 12 Gy/hr), and a very Low Dose Rate vLDR. There is a Medium Dose Rate or hybrid at 2-12 Gy/hr. The rates are expressed in Grays (Gy)/hour which are SI units of energy absorbed from ionizing radiation, equal to the absorption of one joule of radiation energy by one kilogram of matter. Since the inception of brachytherapy at the beginning of the $20^{th}$ century (i.e., soon after the discovery of radiation) delivery has been predominately LDR.

LDR brachytherapy typically delivers radiation at a rate of about 50 cGy/hr (i.e., 0.5 Gy/hr) while HDR typically delivers at a rate of about 0.2 Gy/minute. The instantaneous rate is much higher at each dwell location for HDR brachytherapy as a very active source must traverse the various treatment locations during each treatment.

LDR brachytherapy delivers radiation continuously (as prescribed relatively uniformly throughout the implanted volume), while HDR brachytherapy delivers radiation intermittently over several days. Regardless of the dose rate, a total final dosage of 60 Gy or less is usually delivered to the patient during brachytherapy if it is the sole source of radiotherapy, and a total dose of 20-40 Gy is delivered during brachytherapy when used in combination with other forms of radiation treatment. These scenarios involve temporary implants in which the device is removed after completion of treatment.

Brachytherapy has been used for more than half a century to treat prostate cancer. In this situation, low activity material emitting a low energy is placed next to or within a tumor. Until now these low emitting devices have mostly been left in place permanently except in extraordinary circumstances. The most commonly employed vLDR source (also known as permanent seeds) is Iodine-125 ($^{125}$I) $^{125}$I decays at a low energy radiation of 30 keV and emits radiation at a dose rate of about 0.04-0.1 Gy/hr (4 to 10 cGy/hr) for multiple days up to a nominal year. vLDR is commonly used for cancers in which the radiation source can be placed proximate to or in the neoplasm and left for a significant period of time or permanently, such as when radioactive material or seeds are placed in prostate tumors. Clinicians administer HDR brachytherapy in multiple sessions to improve patient tolerance. Thus, the patient is subjected to the additional risk of multiple procedures, often requiring anesthesia. Patients with cancers within lumen, ducts, or tracts, such as cancer of the esophagus or biliary tract of the liver, have less tolerance for brachytherapy if connections (for example, catheters) are connected externally for multiple days. Such protracted use of catheters often leads to kinking, dislodgement, obstruction, irritation, and the risk of life-threatening infections. (The most commonly employed radio isotopic source is Ir 192 with an energy of 0.38 MEV and half live of 74 days. Cs 137 (T1/2 30.2 years energy 0.662 MEV and Co 60 T1/2 5 years and energy of 1.2 MEV have occasionally been used, mostly in the past.)

HDR employs a primary housing containing a relatively high energy source (about 10 Ci), often as Iridium-192 (0.4 MeV). Treatment sessions last about 30 minutes. HDR is commonly applied in 2 to 3 daily sessions over the course of a few days, or multiple placement of an after-loading catheter in e.g. esophageal cancer treatment with multiple procedures and anesthesia.

Brachytherapy dosage is usually calculated at a fixed distance (or as a volume measuring the MPD or minimal peripheral dose) from the radiation source. HDR requires a highly active source delivering radiation at a dose rate of about 12 to 20 Gy/hr. Hot and cold spots, due to uneven distribution of radiation does, occur with small deviations in distance between the tissue and the radiation source. Thus, brachytherapy treatment using a centralized radioactive material housing or containment can result in significant patient toxicity if the radioactive source is not centralized. For example, for patients with esophagus cancer, potentially life-threatening fistulas occurred at a rate of 12 percent when treated with HDR brachytherapy in the study of Gasper et al,

*International Journal of Radiation Oncology, Biology, Physics* 38 (1) 127-321 (1997). However, there are many reasons for the source to be skewed to one side as even an active tumor could displace the source. Lastly, HDR treatment requires a specially shielded patient room with appropriate radiation precautions. The vLDR applications disclosed in the instant specification do not.

State of the art devices for delivering radiation to internal tissues lack two important essential features: 1) the ability to remove or replace the radiation sources in situ when clinically appropriate, and 2) the ability to change the geometry, energy or radioactive sources of the radioactive particles or seeds in situ according to clinical needs. Typically, once the radiation source carrier(s) and the radiation source(s) is/are placed, they remain permanently within the patient or for the duration of patient treatment. Leaving a permanent radiation source in a patient, where it or its carrier may migrate over time or the tumor may change in shape or size, has the potential undesirable effect that healthy tissue will be exposed to the radiation, while the target cancerous tissue is not. The ability to remove the radioactive sources in this situation or prior to surgery, while clinically useful, is currently lacking from the state of the art, as is the ability to easily localize the brachytherapy treatment or stent in vivo in the doctor's office without requiring formal imaging. In the event of a patient's death, it also may be desirable to remove the sources before cremation or burial.

Additionally, it may be clinically necessary to continue radiation therapy after the activity of the radioactive material has decayed. For example, $^{125}$I has a half-life of about 60 days. If the tumor is still present or grows in size after an initial brachytherapy treatment (which sometimes occurs within six months), then it would be advantageous to replace the depleted radiation source with a source that has higher activity or shorter half-life. This is because new, perhaps faster growing, tumors may be better controlled with radiation that has a shorter half-life or that decays and emits radiation faster. Surviving tumor clones may have different biology and require faster or even slower radiation exposure rates for sterilization. Approximately ninety percent of tumor recurrences are where the original tumor was abutting healthy tissue. However, state of the art methods for delivering radiation at these margin areas after tumor excision has drawbacks. For example, radioactive seed-carrying sutures are sometimes used with absorbable mesh to close up excision sites. But the suture positions shift in time as the mesh is absorbed by the body. This often leads to the sutures sometimes collapsing on themselves, and otherwise not maintaining the optimal seed positioning relative to the neoplasm or vulnerable tissue. Under dosing occurs, leading to recurrence. Conversely, over dosing occurs, leading to injury to healthy tissue.

It would be advantageous to adjust the position and the activity of the radioactive source on its carrier in response to changes in tumor shape and size, carrier position, and other relevant therapeutic factors. It also may be appropriate to remove the radiation sources before surgery or other intervention to reduce personnel exposure or damage to sensitive equipment. Finally, it may be clinically useful to load the radioactive sources sometime after the placement of the device. None of the state of the art addresses provides these features.

Therefore, a need exists in the art for a method and device to deliver radiation and other medicaments to a patient while maintaining the original shape and size of the pre-operative surgical site (e.g., post lumpectomy). The device could be made to mimic the natural feel and bulk of original tissue simultaneous with delivering low level or high level radiation doses. The device should allow for embedment of radioactive particles in a reversibly deformable carrier and post-surgical repositioning of the carrier.

SUMMARY OF THE INVENTION

An object of this invention is to provide a device and a method for delivery medicaments that overcomes many of the disadvantages of the prior art.

Another object of the invention is to provide a device to enable focalized delivery of radiation in patients. A feature of this device is a medicament source supported by a reversibly deformable carrier (RDC). An advantage of the device is that the carrier may be left in place permanently to provide structural support for surrounding tissue during or after treatment and to provide an indicator of the original margins of an excised tumor.

Still another object of the instant invention is to provide a method and device for delivering medicaments to a specific site in the body. A feature of the method and device is that a carrier used to support the medicaments expands to fill the tumor excise site. An advantage of the method and device is that it provides a means for allowing passage of ascetic-, pleural- and other-fluids through the device to contact surrounding tissue. This enables the eradication (destruction, killing, deactivation) of floating tumor cells.

Yet another object of the invention is to provide a reversible deformable receiver for medicaments, wherein the receiver resides within a patient. A feature of the receiver is that it is adapted to support medicaments such as radioisotopes, therapeutic materials, pharmaceuticals, drugs, diagnostic materials, biologically active compounds or materials, or any other medicament, wherein the medicament resides on the outer surface of the receiver, concentrated at a specific region within the carrier, or else dispersed homogeneously throughout the carrier. An advantage of the invention is that the medicament may be applied locally in a focalized manner to target tissues. Another advantage is that the medicament receivers may be modified to facilitate medicament diffusion or movement from the receivers to target tissue once the carrier expands to contact the surfaces of the surgically produced void.

The invention provides a medicament delivery vehicle, the vehicle comprising a reversibly deformable carrier (RDC) adapted to support the medicament on an outside surface of the carrier, an inside surface of the carrier, or homogeneously dispersed throughout the carrier. Specifically, the invention provides a medicament delivery device comprising an RDC adapted to support the medicament. In an embodiment of the invention, the carrier defines a shape to affect an equal radiation dose over its entire external surface. (The shape is specific to each seed in its appropriate geometry.) One such shape is an ovoid. Ovoids facilitate passage of the carrier through a needle and into a tumor mass or site, as what occurs in interventional radiology. During passage, the carrier would be compressed; after passage (when compression forces are removed) the carrier subsequently expands to its predetermined ovoid shape.

Another embodiment of the invention has the carrier shrink in size (such as volume displaced) in proportion to the decreasing strength of the sources. In this embodiment the RDC is comprised of material similar to that which constitutes shrinking sutures and meshes. Suitable shrinkable material is often synthetic and comprised of glycolide and L-lactide and similar moieties. This material is widely commercially available, for example, as Vicryl Rapide (polyglactin 910), manufactured by Ethicon, of San Angelo, Tex.

The invention further provides a method for providing radiation treatment, the method comprising: establishing a tumor excision void in a patient; and filling the void with a plurality of reversibly deformable substrates containing radioactive particles. The invention further provides a system for loading the substrates directly into a catheter, tubing or other conduit, all in vivo. The invention also provides a method for detecting any movement to the substrate once the substrate is placed inside a patient. This movement detection method utilizes ultrasound radio frequency beacon induction localization via an embedded source and Geiger chamber.

BRIEF DESCRIPTION OF THE DRAWINGS

The invention together with the above and other objects and advantages will be best understood from the following detailed description of the preferred embodiment of the invention shown in the accompanying drawings, wherein.

DETAILED DESCRIPTION OF THE INVENTION

Figure 1:
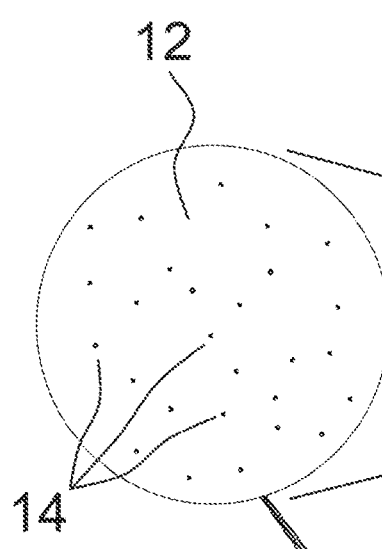
FIG. 1 is an elevational view of a reversibly deformable medicament carrier and medicament, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a three dimensional vehicle for delivering and administering radiation in medical applications. The vehicle serves to both keep radiation dosage consistent during course of treatment, and to keep radioactive particles in the same position they were in when the vehicle was first inserted into the body. While vLDR sources are considered permanent implants, this invention provides an option for replacing the radioactive material while the physical carrier of the radiation source remains at the treatment site.

Generally, the invented reversibly deformable device has the potential to improve treatment for many cancers, by better preserving function, decreasing bleeding, providing palliation, and providing alternative treatments for applications in which surgery is the only available state of the art treatment.

The invention provides irradiated space fillers for cancer treatment, wherein the fillers offer palliation and minimally interfere with radiation or chemotherapy, while potentially decreasing patient toxicity and the incidence of fistulas. Given the nonpermanent (i.e. changeable) shape of the carrier, carrier materials are chosen either to remain constant in volume so as to assure an accurate dose to tissue, or to expand or otherwise change shape in response to environmental stimuli, such as temperature changes, contact with wavelength of certain frequencies, including visible light, ultra sound, laser radiation, heat, and combinations thereof.

A salient feature of the invention is its ability to memorialize or bookmark original tumor sites. In one embodiment, this feature is enabled by the RDCs utilized such that the margin of radiation as initially applied to an excised tumor site corresponds to the margin of the original tumor. For example, the RDC substrate anatomically replicates an excised cancer bed of a patient. Another embodiment comprises the use of a marker or a plurality of markers placed in close spatial relationship to the radiative sources. A first dataset is generated at an initial implant time $t_0$ showing the position of the marker(s) relative to the radiation source and the tumor site. A second and subsequent dataset is generated at second or subsequent time $t_x$ to again show the position of the markers relative to the radiation sources and/or the tumor site. The datasets provide a continuum so as to compare any movement in the implant over time.

The prototypical site for the reversible deformable devices envisioned is for the treatment of breast cancer. These devices are intended to decrease local recurrences, improve survivals and decrease common morbidities including those to the skin, underlying lungs and hearts.

An embodiment of the invention comprises radiation sources (e.g., particles, seeds, capsules containing fluids, or other medicaments) embedded within the RDCs. The RDC provides spacing around the radiation sources. This embodiment prevents an infinitely high dose of radiation being applied to normal tissue. Thus, this embodiment prevents burns. Since there are 1.4 million cases of breast cancer detected annually, this is affordable treatment in areas in which care may be limited.

In another embodiment of the invention, a free forming RDC substrate or scaffold is utilized to hold medicaments (radiation seeds and/or nonradioactive materials) on or close to exterior regions of the RDC surface. (Free forming means that the carrier is molded or formed around the tissue to be treated.) In this embodiment, the radioactive source would be contacting, or in close spatial relationship to a tissue surface volume defining the surgical/excision site. This embodiment would enable more effective treatment of (for example) mesothelioma, peritoneal cancers or meningiomas.

In a third embodiment of the invention, single point source radiation particles are strung together or placed on the surface of a mesh or an RDC. Interior from the surface of that mesh or of the RDC are placed non-radioactive substrates or fluids, those substrates and fluids being radio transparent compared to the particles. These substrates or fluids provide means to fill up the inside of a target tissue volume. This embodiment is placed on a surface such as the pleura or peritoneum to treat malignancies involving those structures. To prevent bleeding in such applications, the carrier would be covered by an agent that promotes clotting, coagulation (i.e. thrombogenesis) and otherwise prevents bleeding. Alternatively, the carrier could be covered with a substance to promote a desired effect, such as antibiotics, anti-clotting material (to prevent adhesions), growth- or other hormones, etc.

The proposed device also decreases adverse toxicities (e.g. bleeding perforations) otherwise caused by sub-optimum placement of the device. As such, the invention minimizes the creation of hotspots and fistulas to tissue, or failures due to cold spots.

The invention supplements the inventor's other treatment modality/paradigm disclosed in U.S. Provisional Patent Application No. 61/692,802, the entirety of which is incorporated by reference. That paradigm features a combination of brachytherapy and stents. The stents provide a means for expanding or opening up a stenotic part of a lumen (e.g., esophagus) which requires treatment, with the seeds residing in the stent. The stent provides a mechanical means of supporting luminal walls and opening ducts or other passageways. However, tumors often grow over or within stents, eventually occluding the lumen and embedding the stent within the tumor The RDC utilized in the instant method and device serves to position medicaments relative to tissues being treated utilizing a reversibly deformable monolith, whereby the monolith comprises the medicament integrally molded or otherwise combined with its carrier. Carriers are selected to maintain the position of radioactive seeds long after the seeds are inserted in the body. This combination provides all of the benefits of high dose radiation therapy with the safety and convenience associated with low dose therapy.

The invention simultaneously allows for the carrier to contain medicament and the entire composite to expand or contract over time, given that vLDR radiation dosimetry is sensitive to geometric factors. Generally, the dose varies as the inverse square of the radiation dose. With isotopes having higher energy, tissue attenuation is slower.

The use of RDCs allows the invented devices to be placed within organ parenchyma, compared to stent carriers which are relegated to luminal structures. As such, the invention provides focalized treatment of specific tissues, including but not limited to cosmetically challenging areas of the breast, neck, face, buttocks, arms, legs and similar shallow tissue venues. The invented modality also treats cancers of deeper venues, including the liver, kidney, adrenal glands, brain, uterus, and bladder, ductile tissues, and the spine. The invention is envisioned to deliver any medicament or therapeutic material, such as radioactive brachytherapy particles, drug solutions, or two-part resins, but is not limited to any specific medicament or class of therapeutic material. These treatment substances and/or their carriers may be remotely activated, by for example emf, magnetic field (i.e., from outside the body), or inducers traveling through the blood stream. Such inducers can include water, engineered nanoparticles, pH changes, ultrasound, x-rays, lasers, temperature changes, and combinations thereof.

The carrier-medicament composites may be inserted through a needle or trocar into the desired site. While straight or curved needles may be utilized, straight needles may facilitate easier loading of medicament-composites comprising radioactive material intercalated with spacers as described infra.

An exemplary embodiment will be described in reference to FIG. 1 as numeral 10. As described supra, the device comprises an RDC 12 which supports medicament 14. The medicament 14 may be supported on an outside surface of the carrier, or homogeneously disbursed throughout the carrier, or concentrated to one particular region or surface (or both) of the carrier 12.

Figure 2:
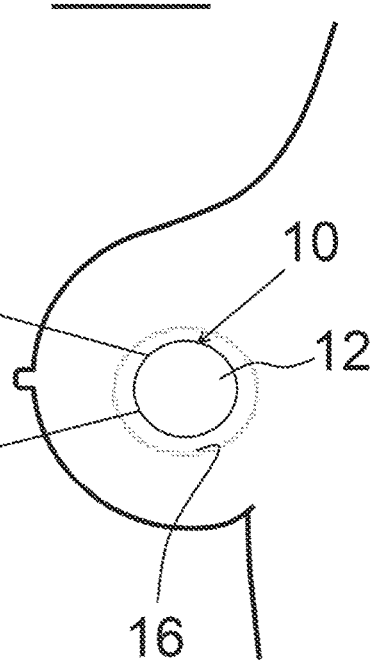
FIG. 2 is cutaway view of the medicament delivery vehicle depicted in FIG. 1, but inserted in a patient, in accordance with features of the present invention.
Figure 3:
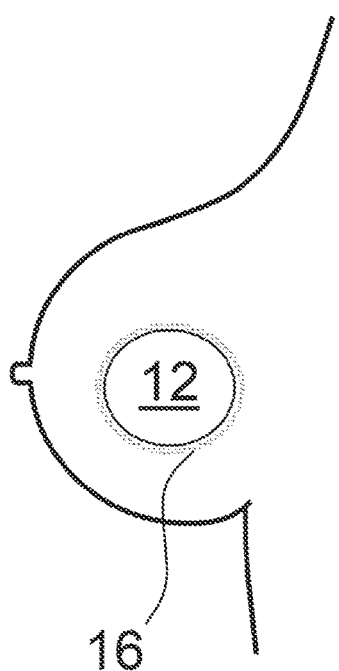
FIG. 3 is a cutaway view of the medicament delivery vehicle positioned in a patient and expanded within a surgical excision site, in accordance with features of the present invention.

FIG. 2 shows the device 12 inserted within a void 16 (depicted in phantom) produced by surgical excision of a tumor. The embodiment shown in FIG. 2 illustrates the carrier 14 as having a volume smaller than the void. This allows for expansion of the carrier to fill the void, this expansion depicted in FIG. 3. Such expansion is effected via any number of environmental cues, such as body temperature, pH, moisture, plasma- or lymph-delivered activating agents (such as water, nanoparticles) or remotely applied stimuli such as externally applied magnetic, electromagnetic radiation, massage, and combinations thereof. For example, the inventor envisions massage as a means for activating expansion activators initially placed into the carrier.

Another embodiment of the invention is of the carrier/medicament composite which is tailored to closely fit the void. In this embodiment, the initial size of the device 12 is that seen in FIG. 3. A means for assuring close fit with the void is to first digitally map the void, then via 3-D printing, generate the carrier.

Carrier Detail

Preferably the RDCs are nonallergenic in nature and bacterially/virally sterile. The texture and feel of the RDCs should be similar to normal tissue. RDCs may be comprised of radiopaque materials, or may be comprised of radio transparent materials, radio opaque materials, and ranges of transparency therebetween, depending upon the application and the need for visualization of the seeds. A preferred embodiment is where the RDC was less radio opaque than the radiation seeds so that the seeds within the RDC can be visualized.

Suitable substrates for RDCs include biocompatible materials as plastic ceramics, polycarbonate ceramic, silicone substrates, foam, and combinations thereof. Optionally, these biocompatible carriers are absorbed by the body over time. Also, carrier substrates are utilized which facilitate rapid heat transfer.

An embodiment of the RDC comprises a multi-component RDC, one component being a flexible scaffold to provide support for a more deformable substrate such as foam. The scaffold provides a means to position the particle a definite distance from the tissue, while the more malleable material positioned between the scaffolding provides a means for conferring a tissue-like feel to the composite. The malleable material also serves to regulate the release of medicament and prevent tumor encroachment. Alternative, the scaffold or spacer is initially left in place, such as in lumpectomies. Subsequently, the scaffold is replaced with a device such as a strut adjusted volume implant (SAVI) or Mammosite through which high dose rate radiation therapy (HDR RT) is delivered.

Preshaped carriers defining a myriad of geometries are suitable, including but not limited to, spirals, spheres, ovoids, planes and other symmetric forms. Planar forms may be necessary to treat larger treatment volumes, such as post surgical scenarios related to lung cancer, pelvic cancer, post meningioma and multiple treatment sites. Asymmetric forms are also suitable, such as where a spiral defines a frusto-conical shape (e.g., exhibiting a narrow diameter at one end and a larger diameter at a second end).

In an embodiment of a treatment protocol utilizing the device, treatment spaces are filled by a plurality of the invented devices as opposed to one or two devices expanding to fill the treatment space. In a preferable application, the devices are used in sites in which the tumor forms a spheroid and where the tumor is usually destroyed by ultrasound, radiofrequency or through debridement. In liver metastasis, the RDCs are positioned so as to fill up the space and the tumor is treated by the radio isotope.

Other suitable cancer venues include the kidneys, brain meninges, lung masses, nodes, prostate, bladder, uterus, ovary, peritoneal cavities and plural cavities.

The RDC-seed composite is fabricated so that the surface dose of the composite is fairly uniform. This will help with dosimetry when calculating dosages.

In an embodiment of the invention, volume of the carrier often can vary from 0.5 cc to 5 cc, and shaped to approximately the radiation distribution of the seed which is supported by the carrier. The seed is positioned at the center of the ovoid-shaped RDC which may have the consistency of local tissue. Several means for inserting the seed into the RDC is available, including radiation shielded gloves, surgical tools, pliers, etc. Seeds are attached to the exterior of RDCs via adhesive.

In instances of vLDR applications (wherein low energy seeds are utilized) the seeds are placed close to the surface of the carrier (e.g., within about 0.1 to 1 cm, and preferably within about one half of a centimeter.) In an embodiment of the invention, an inert spacer (either radio transparent or radio-opaque) occupies the center of the treatment volume and is surrounded by radioactive RDCs.

Medicament Detail

A myriad of medicaments are envisioned for use in combination with the RDC. Medicament types include radioactive substrates such as brachytherapy seeds, and radioactive fluids. Suitable radio isotopes for permanent seed applications include, but are not limited to, I 125, Pd 103, Cs 131 and Yb 169. All of these sources discharge low energy photons (e.g., from 22 keV to about 100 keV). The range of the radiation depends on geometry especially inverse square law but also adsorption in tissue and air. Individual seeds are shielded by the encapsulation process which usually limits the useful exposure to a short range of x or gamma rays. The initial dose rate would vary inversely with halve life. As an example the typical initial dose rate for an I 125 prostate implant would usually be about 0.07 Gy/hr (7 rad per hour as opposed to about 20 for Palladium 103. Host factors such as oxygenation, intrinsic radiosensitivity proliferation rate repair capacity are more difficult to control.

A suitable brachytherapy seed is available from a myriad of commercial sources, including the Proxcelan™ Cesium 131, manufactured by IsoRay Medical in Richland Wash. Generally, such radioactive particles are provided non-sterile and must therefore be sterilized prior to insertion into the carrier. As such, preferably, the carrier is also capable of being sterilized.

Also as noted supra, the carrier is adapted to receive medicaments. In an embodiment of the invention, the carrier/medicament composite structure is a vehicle for treating cancers and areas of the body invaded by neoplasms. A myriad of radioactive particles are suitable medicaments for being supported by the carrier. Exemplary such particles include, but are not limited to, isotopes such as currently available $^{125}$I, Ytterbium-169, Palladium-103, or Cesium-131. $^{125}$I is a suitable source for vLDR applications, given its relatively short half-life (about 60 days) and relatively low energy (about 30 keV).

Generally, suitable medicaments are those that are capable of being supported by the carrier. Interaction between the medicament and the carrier can be via adsorption, hydrophilic or hydrophobic interaction, covalent attachment, ionic attachment, or even via adhesive in the case of radioactive particles. Also, the carrier may be combined with radioactive material via bombardment with a radioactive ion whereby variation of the voltage applied and carrier surface area exposed determines the radioactive voltage. It is envisioned that the RDCs, residing in a tumor excision site will absorb fluid radioisotope, such as samarium. This will prevent leakage of the isotope, and miscalculation of dosage which otherwise would occur if the radioisotope is simply infused into the tissue space.

In an embodiment of the invention, the seeds themselves are not provided in raw state, but rather jacketed in radio-transparent material such as titanium, platinum, tungsten steel, alloys thereof, and combinations thereof. Decay products such as alpha particles, beta particles, auger electrons, Internal Conversion electrons, x rays, and gamma rays are mostly absorbed by the seed encapsulation.

Often, the radioactive material is adsorbed onto an inorganic substrate, such that the substrate and the radioactive seeds are both encased in the radio-transparent material. Also, radioactive seeds may be separated from each other by the structure of the carrier.

Suitable radioactive particle sizes are those which can be loaded into the RDC. Typical sizes have diameters beginning at about 0.4 mm and a length of about 4 mm (Iodine-125 "thin seeds" from GE/Oncura, or Ytterbium-169 particles from SPEC). Typical particle (e.g. seed) diameters and lengths range from about 0.4 to about 1.2 mm in diameter and 0.4 to 1.2 mm in length. Smaller size particles allow for easier placement of the instant invention in small-volume lumen, such as the biliary tract of the liver.

An embodiment of the fabrication method for producing the carrier-medicament composite combines commercially available seeds with RDCs. This protocol provides more accurate calculation of the resulting radiation doses compared to techniques which comprise "doping" carrier substrate (such as silicon) with radiation.

The seeds may be added to the carrier individually or else first chained together and added to the carrier. Generally, the seeds range in size from about 1 mm to 15 mm in length, preferably from about 4 to 8 mm, and most preferably about 6 mm. An embodiment of the invention is where the carrier completely encapsulates the seeds.

The instant invention is not limited to the use of radioactive particles. Liquid solutions, pharmaceuticals including radio-pharmaceuticals, dissolvable solids, capsules containing liquid drugs, or other desired material may be included within the RDCs. These medicament particles or materials may also be separated by spacers to provide and maintain the geometry and dosage of the medicament throughout the RDCs, according to clinical need. For example, if a drug solution is to be applied to a desired portion of the tissue, then a drug delivery particle may be localized to this region by inclusion of spacers for the remaining volume of the carriers.

Other medicament types include antibiotics, chemotherapeutic agents, coagulants, thinners, and constituents of these medicament types. As the porous carrier is in fluid communication with blood, lymph, and other fluids circulating through the body, medicaments attached to the carrier can be activated by agents delivered via natural fluid transfers of the patient. RDCs which are porous in nature to facilitate fluid transfer through the RDCs is disclosed.

The term medicament need not be restricted to therapeutic materials, but also materials for other clinical purposes. For example, the tubular members may comprise radiopaque substrates that allow for diagnostic imaging of the location of the tubular members or patient anatomy. Specifically, the instant device may be modified to deliver medicaments such as radiopharmaceuticals, radiotracers, or contrast agents for possible applications such as Computed Tomography (CT), Single Photon Emission Computed Tomography (SPECT), or Magnetic Resonance Imaging (MRI). A focalized application of such medicaments may be desirable for diagnostic imaging or other clinical applications because the substance may be at a desired local concentration without unnecessary exposure of non-target areas such as occurs with systemic administration.

Other medicaments that may be used with the instant device include but are not limited to small interfering RNA (siRNA), DNA used for gene therapy, monoclonal antibodies targeted to relevant receptors, growth factors such as the Insulin-like Growth Factors (IGFs), radiolabeled nanoparticles, or medicaments which are chemically targeted to desired tissues or areas.

In an embodiment of the invention wherein non-radioactive medicaments are utilized, porous RDCs have their surfaces treated with a moiety for reversibly attaching medicaments to those surfaces. Such medicament detachment occurs with changes in pH, the presence of water, chelating agents, or outside stimuli such as radiation (e.g., external beam radio chemotherapy) or physical massage. Medicament can be homogeneously dispersed through the carrier by capillary action, pressure, vacuum pull, or simple soaking for a predetermined time in a fluid containing the medicament.

Example 1

A preferred embodiment is the use of shaped soft tissue equivalent carriers in which a permanent radioactive seed is centrally spaced (or otherwise optimally spaced viz the effected tissue). Palladium and Iodide seeds are the most attractive commercially available radio isotopes. The seeds placed in such a carrier are homogeneously (i.e. evenly) spaced when subsequently placed within a target volume. Bunching of sources in a specific area and other volumes in which there is a paucity of sources is avoided.

A suitable material would have similar consistency of the normal tissue it is replacing (such as breast), and be hypo allergenic. This material would not leak and would have an appropriate geometry. In the breast cancer scenario, RDC material would have a radio isotope seed buried within its center (i.e., in a specific central area). Also, the RDC defines a shape similar to the dose pattern of the radioisotope seed utilized. This prevents over exposure and uneven dosages to the tissue requiring treatment.

The shape of the carrier is modified by the seed actual dosimetry. In the case of cesium, the radioactive source within the seed may be no more than 0.5 cm from the surface of this applicator. In an embodiment of the invention, the entirety of the radioactive applicators are surrounded by a mesh to prevent displacement. Also, in an embodiment of the invention, the surface of the individual applicator is not within 8 mm of the skin surface to avoid a high surface radiation dose.

Spacers comprised of inert material can be used to separate and or link seeds together. The spacers provide a means to maintain the desired geometry of the radioactive particles relative to each other, and to the tissue being treated. The spacers may be free flowing and radio opaque to serve as a diluent, or else radio-transparent and attached to the particles flanking them, those flanking particles being radioactive particles, additional spacers or combinations thereof. These spacers may include markers or other nonradioactive materials such as metals (e.g., gold, other nonferrous material, ferrous material), nonmetals (e.g., plastics, fluidized chemical moieties) which can be further used to modify the plume of radiation emanating from the seed, and also to assist in determining the position of implanted radiation sources relative to each other, to the marker, and to the original tumor site.

The markers may comprise sutures, particles homogeneous dispersed within the radiative source, capsulized fluids (scintillation fluids), and discrete objects and shapes placed at predetermined points either on or within the RDC or tumor excise site. In one embodiment, the markers are placed as staples, which typically define a periphery of a tumor excise site.

The diameter of the RDCs and the sizes of the particles contained therein will be constrained by the volume of the target lumen. As such, the diameter will be empirically determined upon receiving imaging data as to actual structural size of the effected tissue. Often the distance between the outside surface of the RDC and the margins of the tumor site (where healthy tissue is found) is between about 0.5 and about 1 centimeter. Upon first inserting the RDC, this distance is accurately determined and compared at a subsequent time to determine if any movement within the body or within the excision site, has occurred. Methods for imaging movement include CT scans, Geiger counters, x-rays, fluorescence induced by radiation including magnetic fields, visible light, IR- and UV radiation, radiofrequency radiation, alpha-, beta-, and gamma-radiation.

As noted supra, the medicament particles and spacers may be connected via a spacer or may be freely dispersed in the carrier. In one embodiment, a linker made of a polymer or other suitable material is used to connect adjacent particles and spacers. In another embodiment, the substrate may be an adhesive, resin, or other material which binds adjacent particles and spacers together. In another embodiment, there may be a continuous substrate contained within the carrier foam that extends along a specific region of the carrier. In this embodiment, the substrate and embedded materials may then slide out of the RDC.

An endoscope can be used to load or replace the radioactive particles in situ by delivering the radioactive particles through a delivery catheter or loading tool. The endoscope is also used to deliver other medicaments such as drug solutions by use of a delivery catheter or loading tool.

The radioactive particles may be removed or replaced according to therapeutic need. For example, the tumor may shrink or change its shape or the carrier's position may migrate in situ. The position of the radioactive particles relative to the target tissue can be adjusted by changing the order and position of the spacers and radioactive particles in situ at a later time after device insertion. Alternatively, if the reversibly deformable material contains ferrous material, the carrier may be manipulated by an externally applied magnetic field.

Shielding material may be included at one surface of the RDC so as to prevent undesired radiation exposure of certain tissue. Tungsten (or titanium) may be used with Iodine-125. In one embodiment, the shielding material may be attached to the RDC. In other embodiments, the shielding material may be attached to one side of the radioactive particles or amalgam of particles. This shielding material may be used to prevent exposure of healthy or other tissue in which it is not desirable to expose the tissue to radiation.

The instant invention may comprise modifications to facilitate the placement and removal of medicament particles. In one possible embodiment, brachytherapy particles and spacers may be coated, for example with wax or silicone, to allow easier translocation into and out of the RDCs. In another embodiment, the RDCs may be reinforced with additional elements to maintain their shape, and keep their hollow center open in instances where medicament is arranged around those centers.

The present invention prevents hotspots by maintaining a more consistent distance between the radiation source and the tissue wall. Thus, the invention enables a vLDR source attached to a RDC, where the radiation source is held on the periphery of the carrier to conform to anatomical curvatures. Thus, large deviations in distance between the tissue and the radiation source do not occur as they do for HDR centralized catheter treatment. Additionally, tumors of longer length can be treated with a vLDR source attached to a RDC. If hot spots are unavoidable because of geometry, the deformability of the carrier allows placement of the hot spots within a tumor. The invention provides a system of treating the metastasis site but without exposing healthy surrounding tissue with permanently embedded radiation sources. In this embodiment, a radiation source is attached to or placed within a RDC which is expanded against the lumen wall, wherein the geometry of the radioactive particles is determined and preserved by separation of the particles with spacers. This would allow for particle position to be customized to maximize delivery to the tumor and minimize exposure to healthy tissue.

Three dimensional configurations of a tumor are ascertained by imaging and the precise position of loose or connected radioactive particles is calculated based on desired radioactive dosages in three-dimensional space. Details for such imaging are known and can be found in Langley et al, 2012, *BJU International,* 109, 1-6, the entirety of which is incorporated by reference. The use of these methods to determine particle position within tubular members positioned against the inner wall of a body cavity, such as a vertebral cavity during kyphoplasty, allows for a customized delivery of radiation, representing a significant improvement of delivery of radiation to tumors located on the wall of endoluminal spaces. Particle activity and position can be calculated based on information from imaging (such as X-ray or CT scans) or other means.

The invention provides a system whereby a removable vLDR radiation source is attached to a RDC, wherein the radiation source can be left in the patient for longer periods, and can be removed or replaced if required. The ability to removably position vLDR radiation sources via expandable carriers confers advantages over current HDR methods using a central catheter, as 1) the vLDR source would be held in direct apposition to the target tissue by the stent, 2) it could be left for an extended period of time in the patient, and 3) the radiation source could be removed and replaced according to clinical requirements, for example changes in tumor shape and size. Additionally, the presence of a vLDR source would improve the mechanical relief of dysphagia by the RDC, as the vLDR would prevent the tumor from growing over the carrier. The proposed device would allow for a removable vLDR radiation source that could be removed and replaced by relatively non-invasive surgical means, such as endoscopy.

Example 2

A specific treatment protocol comprises preparing a plurality of RDC/radioisotope composites in the shape to mimic the radiation dose emanating from a naked radioisotope particle. For example, radioisotope particles that are rod shaped emit higher doses of radiation along their length compared to at their ends. As such, a suitable RDC encapsulating these particle shapes would be more ovoid so that radiation doses permeating through them are similar over the entire surface of the RCC. Other suitable shapes include spheres, spirals, planar structures, and combinations thereof. The composites are then delivered to the surgical theatre such as the operating room, wherein the composites are positioned within a lumpectomy site, or other such local resection site.

A first step in the process is to place a balloon spacer within a lumpectomy site in order to complete the pathological evaluation of the patient for treatments. The evaluation includes calculating the distance of a radiation source to the skin covering the outside of the body. Once this evaluation is complete, a plurality of approximately 1 cm ovoid devices with a radioactive seed emplanted therein supplant the volume maintained by the balloon. Alternatively, the devices are inserted within the balloon itself which remains inflated.

In an embodiment of the method for treating cancers, the rad seed containing carriers are inserted into the lumpectomy or other surgical site such that the carriers are contacting existing carriers, and also the tissue defining the surgical site. In this embodiment, the plurality of such carriers define inner regions such that some of the carriers are contacting only other carriers, and exterior regions whereby the carriers are contacting other carriers and also body tissue defining the "healthy" periphery of the surgical site. One means for maintaining the position of the plurality of RDCs stuffed into the site is to first insert the RDC/isotope composite into a mesh bag, which in turn is inserted into the surgical excision void. Another means for maintaining the position of RDCs is to adhere the RDCs to the outside surface of the bag, balloon or other inert volume filling substrate.

Figure 4:
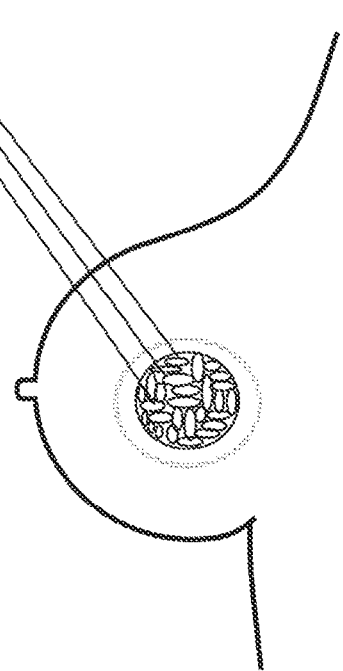
FIG. 4 is a cutaway view of a plurality of medicament delivery vehicles positioned in a surgical excision site, in accordance with features of the present invention.

FIG. 4 is a schematic of this treatment protocol. As noted supra, the spheroids have a shape such that the dose at or near the surface would be uniform to correspond to the dosage emanating from the rod-shaped radioactive particles the spheroids encase. However a larger or different shape could be constructed in which the surface or surfaces would have RDC's or equivalence placed on them. For example, a central spheroid is envisioned as a support for the relatively smaller approximately 1 cm spheroidal RDCs placed uniformly on the central spheroid. Also envisioned is the use of spiral-clad particles supported by RDCs.

Example 3

An embodiment of the carrier/radioisotope composite resembles a slab or planar substrate. Such a planar implant (useful for treating meningiomas) comprises a reversibly deformable tubular substrate shaped into a slab to define a substantially two-dimensional entity. Radioactive particles are attached onto outside surfaces of, or alternatively inserted into, the so-shaped tubular substrate. Suitable tubular substrate is comprised of at least partially radio-transparent material such as plastic, memory nitinol. This configuration would have a fixed geometry.

Possible applications for this example include treatment of neoplasms of the neck, chest, abdomen and pelvis.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

What is claimed is:

1. A delivery device for providing radiation treatment, the delivery device comprising a reversibly deformable substrate coupled to a flexible scaffold, wherein the reversibly deformable substrate is positioned between the flexible scaffold; and
    a plurality of radioactive seeds removable from the reversibly deformable substrate in situ;
    wherein the scaffold, the reversibly deformable substrate and the plurality of radioactive seeds are positionable within a void in a patient's body,
    wherein the plurality of radioactive seeds are configured to be replaced in situ while the scaffold and the substrate remain in the void, and
    wherein at least a portion of the radioactive seeds are supported on an outer surface of the substrate.

2. The device as recited in claim 1, wherein the radioactive seeds are surrounded by the substrate.

3. The device as recited in claim 1, wherein the substrate is configured to anatomically replicate an excised cancer bed of a patient.

4. The device as recited in claim 3, wherein the substrate is adapted to expand to fill the void defining the cancer bed.

5. The device as recited in claim 4, wherein the substrate is adapted to expand when manipulated from outside of the patient.

6. The device as recited in claim 4, further comprising a plurality of delivery devices, wherein each device comprises a reversibly deformable substrate adapted to support a plurality of radioactive seeds, and wherein the plurality of devices are configured to reside in the void.

7. A medical device for providing radiation treatment, the medical device comprising:
    a flexible scaffold;
    a plurality of radioactive seeds;
    a reversibly deformable substrate positioned between the flexible scaffold, wherein the substrate is designed to removably receive the radioactive seeds for placement within a void in a patient's body; and
    at least one spacer positioned adjacent the plurality of radioactive seeds;
    wherein the plurality of radioactive seeds are removable from the reversibly deformable substrate in situ while the scaffold and the substrate remain in the void, and
    wherein at least a portion of the radioactive seeds are supported on an outer surface of the substrate.

8. The device as recited in claim 7, wherein at least a portion of the reversibly deformable substrate surrounds the radioactive seeds.

9. The device as recited in claim 7, wherein the substrate is configured to be manipulated from outside the patient.

10. The device as recited in claim 7, wherein the reversibly deformable substrate is configured to expand and fill the void within the patient.

11. The device as recited in claim 7, further comprising means for monitoring a movement of the reversibly deformable substrate within the void over time.

12. A radiation delivery device, comprising:
    a flexible scaffold;
    a reversibly deformable substrate positioned between the flexible scaffold;
    a plurality of radioactive seeds positioned in the reversibly deformable substrate;
    wherein the reversibly deformable substrate and the scaffold are positionable within a void in a patient's body with the plurality of radioactive seeds positioned in the reversibly deformable substrate; and
    a plurality of radiopaque markers dispersed along the reversibly deformable substrate;
    wherein the plurality of radioactive seeds are removable from the reversibly deformable substrate in situ while the substrate remains in the void, and
    wherein at least a portion of the radioactive seeds are supported on an outer surface of the substrate.

13. The device of claim 12, further comprising at least one spacer, wherein the spacer is configured to link the plurality of seeds together.

14. The device as recited in claim 13, wherein the at least one spacer includes at least one of the radiopaque markers.

15. The device as recited in claim 12, wherein the markers are arranged within a single plane.

16. The device as recited in claim 12, wherein the markers are arranged within multiple planes.

17. The device as recited in claim 12, wherein the plurality of radiopaque markers are homogeneously dispersed throughout the reversibly deformable substrate.

18. The device as recited in claim 12, wherein the plurality of radiopaque markers reside on an outside surface of the reversibly deformable substrate.

* * * * *